United States Patent [19]

Zavislan et al.

[11] Patent Number: 5,860,967
[45] Date of Patent: Jan. 19, 1999

[54] DERMATOLOGICAL LASER TREATMENT SYSTEM WITH ELECTRONIC VISUALIZATION OF THE AREA BEING TREATED

[75] Inventors: James M. Zavislan; Jay M. Eastman, both of Pittsford, N.Y.

[73] Assignee: Lucid, Inc., Henrietta, N.Y.

[21] Appl. No.: 94,296

[22] Filed: Jul. 21, 1993

[51] Int. Cl.$^6$ ...................................... A61N 5/02
[52] U.S. Cl. .................. 606/9; 606/10; 606/12; 607/89
[58] Field of Search ............... 606/9–13, 16–18; 607/89

[56] References Cited

U.S. PATENT DOCUMENTS

| | | |
|---|---|---|
| 3,538,919 | 11/1970 | Meyer . |
| 3,693,623 | 9/1972 | Harte et al. . |
| 3,834,391 | 9/1974 | Block . |
| 4,289,378 | 9/1981 | Remy et al. . |
| 4,388,924 | 6/1983 | Weissman et al. . |
| 4,617,926 | 10/1986 | Sutton . |
| 4,733,660 | 3/1988 | Itzkan ........................................ 606/9 |
| 4,786,155 | 11/1988 | Fantone et al. . |
| 4,901,718 | 2/1990 | Bille . |
| 5,059,192 | 10/1991 | Zaias . |
| 5,112,328 | 5/1992 | Tabaoda et al. . |
| 5,336,217 | 8/1994 | Buxs et al. .................................. 606/9 |

OTHER PUBLICATIONS

Selective Photothermolysis: Precise Microsurgery by Selective Absorption of Pulsed Radiation, "Science," vol. 220.
The IRIS Medical Diode Laser Indirect Ophthalmoscope OcuLight® SLx Diode Laser System.
The OcuLight® SL Diode Photocoagulator IRIS Medical Endo Probes™.
Keeler Ophthalmic—Cover Page, pp. 1–4 & back of cover
Hexascan Brightens the Future for Millions of People.
The Lihtan Hexascan™ CVL Network News—Spring 92.
Metalaser Technologies—Network News, Winter, 1992.
Metalaser Technologies—Network News—Winter 92.
Autolase™ Scanner—1991 Metalaser Technologies, Inc.
Clinical Summery of Copper Vapor Laser Treatment of Dermatologic Disease: A Private Practice Viewpoint—Harold A. Lancer, M.D., F.A.A.D.

*Primary Examiner*—Michael Peffley
*Attorney, Agent, or Firm*—M. Lukacher; K. Lukacher

[57] ABSTRACT

A hand held microsurgical instrument for applying laser energy to selected locations (sites) in an area under the skin (or other exposed translucent tissue) to provide localized photothermolysis of underlying tissue at these sites, is described. The laser energy is focused into a spot within the tissue. This spot is of sufficiently small size so that the energy density is sufficient to provide surgical or treatment effects within the tissue without damaging the surface tissue. In dermatology, for example, the technique can be used to destroy endothelial cells in blood vessels which are desired to be removed, such spider veins (nevi) in the skin, hair follicles to prevent hair growth therefrom, or other microsurgical procedures. The area is visualized while the laser beam is steered, using a deflection system, in X and Y coordinates. A telecentric optical system, in which a mirror of the deflection system is located, directs the laser light essentially perpendicular to the area to be treated as the beam is scanned over the area. The optical system also focuses illumination light reflected from the area to a sensor matrix of a CCD video camera. The reflected illumination light is imaged essentially parallel to the optical axis in the object space thereby providing a precise, high resolution image corresponding to the area. The laser beam may be tracked as it is deflected over the area to the selected locations by visualization thereof on a display or monitor associated with the video camera. The locations are then apparent to the treating physician who can then effect an increase of the beam power or turn the beam on so as to treat the tissue in the selected locations.

30 Claims, 9 Drawing Sheets

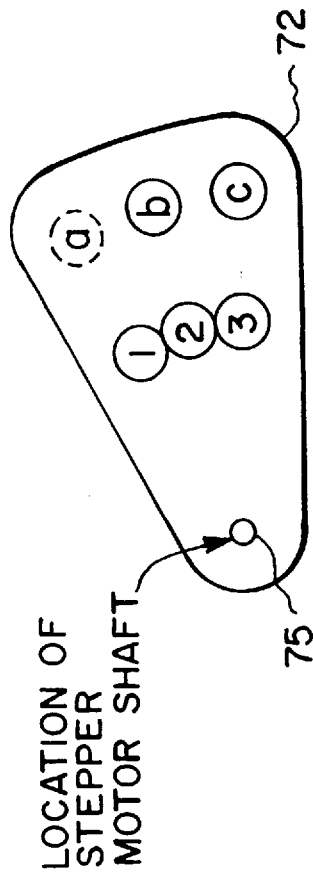

1 = LOCATION OF IR TRANSMITTING OR BLOCKING FILTER FOR VIEWING SYSTEM

2 = LOCATION OF OPEN HOLE (VISIBLE I/R VIEWING)

3 = LOCATION OF NEUTRAL DENSITY FILTER TO PROTECT CCD ARRAY DURING THE TREATMENT PULSE a = LOCATION OF DENSE BLOCK AND PHOTODETECTOR FOR THE LASER LIGHT b = LOCATION OF NEUTRAL DENSITY FILTER TO PRODUCE LASER "SPOTTER BEAM"

c = LOCATION OF OPEN HOLE FOR BEAM TREATMENT

*FIG. 5*

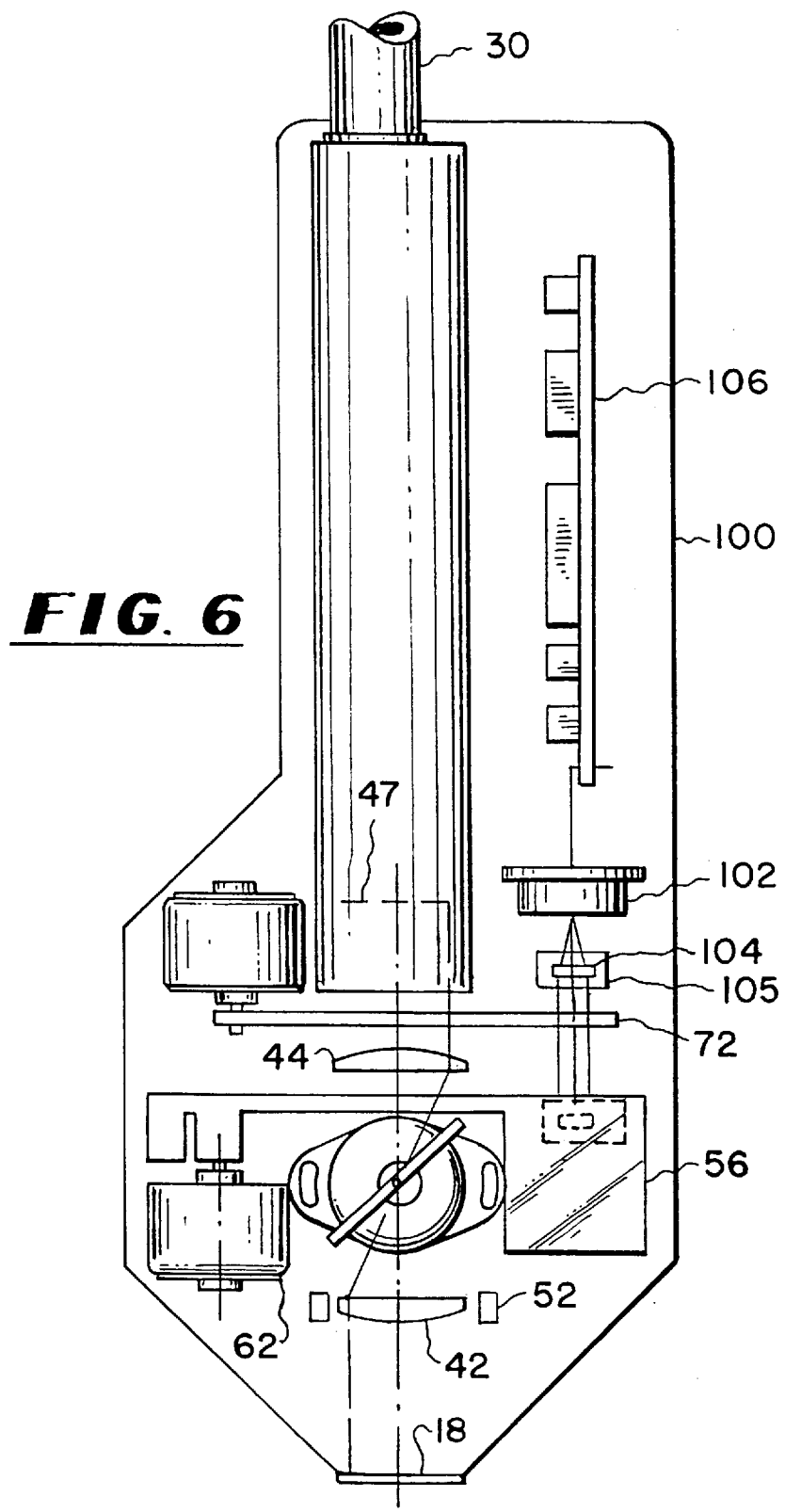

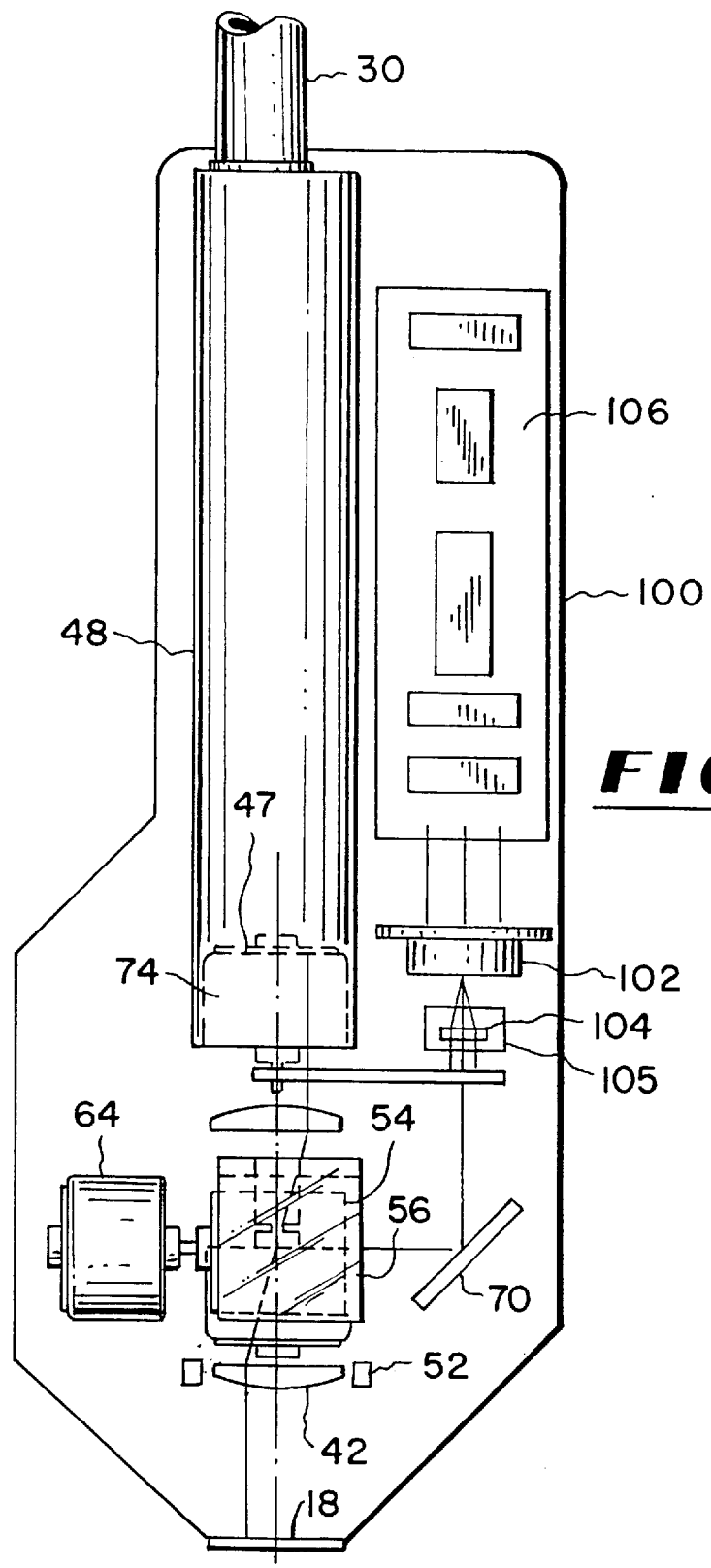

DERMATOLOGICAL LASER TREATMENT SYSTEM WITH ELECTRONIC VISUALIZATION OF THE AREA BEING TREATED

The present invention relates to a system (method and apparatus) for carrying out microsurgical treatments especially in dermatology and particularly for surgery in selected locations under the surface of the skin or other exposed translucent tissue.

The present invention is especially suitable for providing a hand held instrument from which a laser beam projects. The beam is focused by optics in the instrument at spots within an area selected for treatment and is deflected across the area while the area is visualized using an electronic visualization means which provides, with the beam focusing optics, an image corresponding to the area under treatment. The deflection of the beam is controlled during visualization to place the focus (a spot) at the selected locations. Then the beam power may be increased or the beam turned on, as with a shutter or with means such as filters in the shutter, which can alterably attenuate the beam, while the beam is being located at the treatment sites. These sites may be along the veins such as spider veins which are photothermolyzed and undergo coagulation necrosis. Hair follicles can also be photothermolyzed so as to cause depilation. Other microsurgical procedures, such as to break adhesions between tendons and the surrounding sheath may be carried out using the invention.

Devices for medical treatment have been provided which use laser beams. Also handpieces from which laser beams are projected and manually traced over the skin, which may be compressed under glass slides for protection and heat dissipation purposes, are available. Such devices and treatment techniques generally use laser energy of a wavelength which makes it effective for treatment of lesions, because the lesions selectively absorb that wavelength. The general area containing the lesion is effectively flooded with generally collimated laser light of a wavelength that is highly absorbed by the lesion or the laser beam is moved over the area. Selective absorption of the laser light by the lesion is then responsible for photothermolysis. This technique is called selective photothermolysis and is discussed with respect to the skin in an article by R. R. Anderson and J. A. Parrish which appeared in *Science,* Vol. 220, p. 524, on Apr. 29, 1983. Also, the wavelengths of the laser illumination for selective photothermolysis are subject to scattering and diffusion by the skin. Accordingly, the area exposed to the radiation is heated and may be subject to collateral damage (i.e. reddened or even burned). This produces discomfort to patients and militates against the use of such laser treatment instruments and techniques.

Laser beams have been used for ophthalmological surgery. In such cases, the medium is transparent to the laser beam and can be readily observed through the cornea with ophthalmoscopes. The lens of the eye undergoing treatment may be used to focus the laser beam on the retina. Often the laser beam is manually directed and considerable skill and technique is required for such laser surgery especially to avoid damaging tissue around the site to be treated. It is therefore difficult to precisely deliver the laser energy to the desired sites. See Taboda, U.S. Pat. No. 5,112,328 issued May 12, 1992, for an ophthalmological laser surgery instrument.

The difficulties encountered in laser microsurgery include the lack of a natural focusing mechanism in non-ocular tissues. Also, penetration of the beam so that it is focused and not diffused into a ball shape volume of area too large to concentrate the energy to the level necessary for treatment is faced in all non-ophthalmological laser surgery devices. Also, such devices have not been provided with a visualization system operating at a wavelength appropriate for imaging through turbid, translucent tissue such as skin and other non-ocular tissue, and with sufficient resolving power to enable location of the beam at the selected site where treatment is desired. There have been some suggestions in the area of ophthalmological instruments, but a system including an instrument for other non-ocular microsurgical treatments has not been provided.

It is the principal object of the present invention to provide an improved system for laser assisted microsurgical and especially dermatological treatments in which the treatment area can be visualized while the laser beam is being located at sites in the area where treatment is desired.

It is another object of the present invention to provide an improved system for microsurgery which is automatically operative both for visualization and for location of the laser beam at treatment sites in an area under the skin or other exposed translucent tissue.

It is a still further object of the invention to provide an improved system for microsurgical treatment which utilizes optical energy which is not readily scattered and which can be focused into a spot of sufficiently small area to concentrate the laser beam so that it reaches a level sufficient to provide a photomedical treatment effect.

It is a still further object of the present invention to provide an improved system for microsurgery, especially dermatological surgery which enables coagulation necrosis of spider veins, depilation by cauterization of hair follicles and allows adhesions between tendons and the surrounding sheath to be severed.

It is a still further object of the present invention to provide an improved microsurgery and especially dermatological surgery system using a laser beam of a wavelength which is effective for photothermolysis by virtue of being focused at sites where photothermolysis is desired rather than relying upon selective absorption by chromophores which are selectively absorptive of different wavelengths of optical energy, thereby providing a single instrument using a single wavelength laser beam for different microsurgical and dermatological treatments.

It is a still further object of the present invention to provide an improved system for microsurgery in which heating and burning of the skin or other tissue in the general area being treated is minimized.

It is a still further object of the present invention to provide an improved laser surgery instrument in which an accurate high resolution image is obtained for visualizing and enabling the direction of the beam to selected sites in the area being treated.

Briefly described, a system for thermolysis of tissue in an area under the surface of the skin or other tissue with visualization of the area which is provided in accordance with the invention may be embodied in a housing which is sufficiently small to be hand held. A window in the housing provides a port for illumination of the area under treatment as well as through which the treating laser beam projects. The laser beam may be provided by a laser external of the housing which is introduced into the housing through an optical fiber cable, an articulated optical delivery arm or by a laser, such as a solid state laser (e.g. a laser diode) which is mounted in the housing. The housing contains optical means for projecting and focusing the beam at selected locations or sites in the area at spots sufficiently small in cross-section, for the power and duration of the beam, to cause localized thermolysis of the tissue at the sites to be treated. There are means in the housing for deflecting the beam to locate the spot at the selected sites one at a time. The housing also has means for visualizing the area while the beam is being deflected, thereby verifying that the spots are at the selected sites before the beam is turned on or its energy increased to cause thermolysis.

The foregoing and other objects, features and advantages of the invention, as well as presently preferred embodiments thereof, will become more apparent from a reading of the following description in connection with the accompanying drawings in which:

FIG. 5 is a top view of the shutter of the instrument shown in FIGS. 3 and 4;

FIG. 6 is a view similar to FIG. 3 wherein a laser diode and associated circuitry is used internally of the housing;

FIG. 7 is a view similar to FIG. 4 of the instrument shown in FIG. 6;

Figure 2:
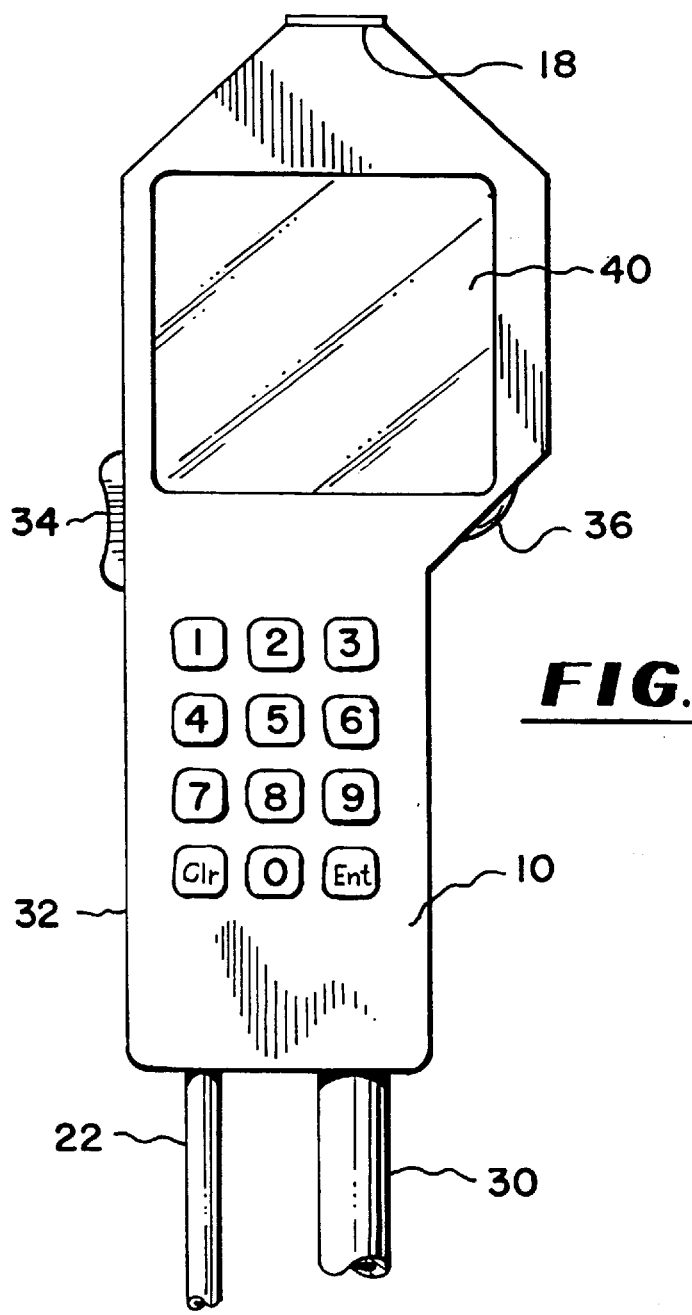
FIG. 2 is an enlarged view of the handpiece (the hand held instrument) of the system shown in FIG. 1.
Figure 8:
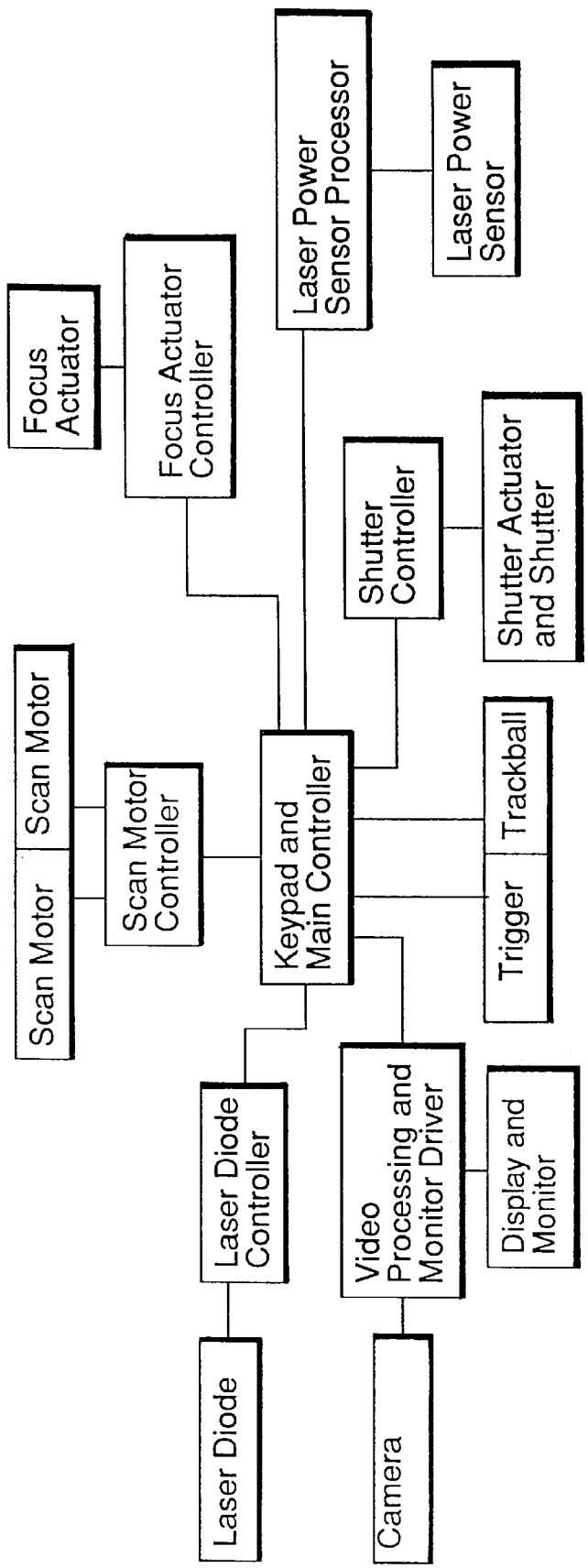
Figure 9:
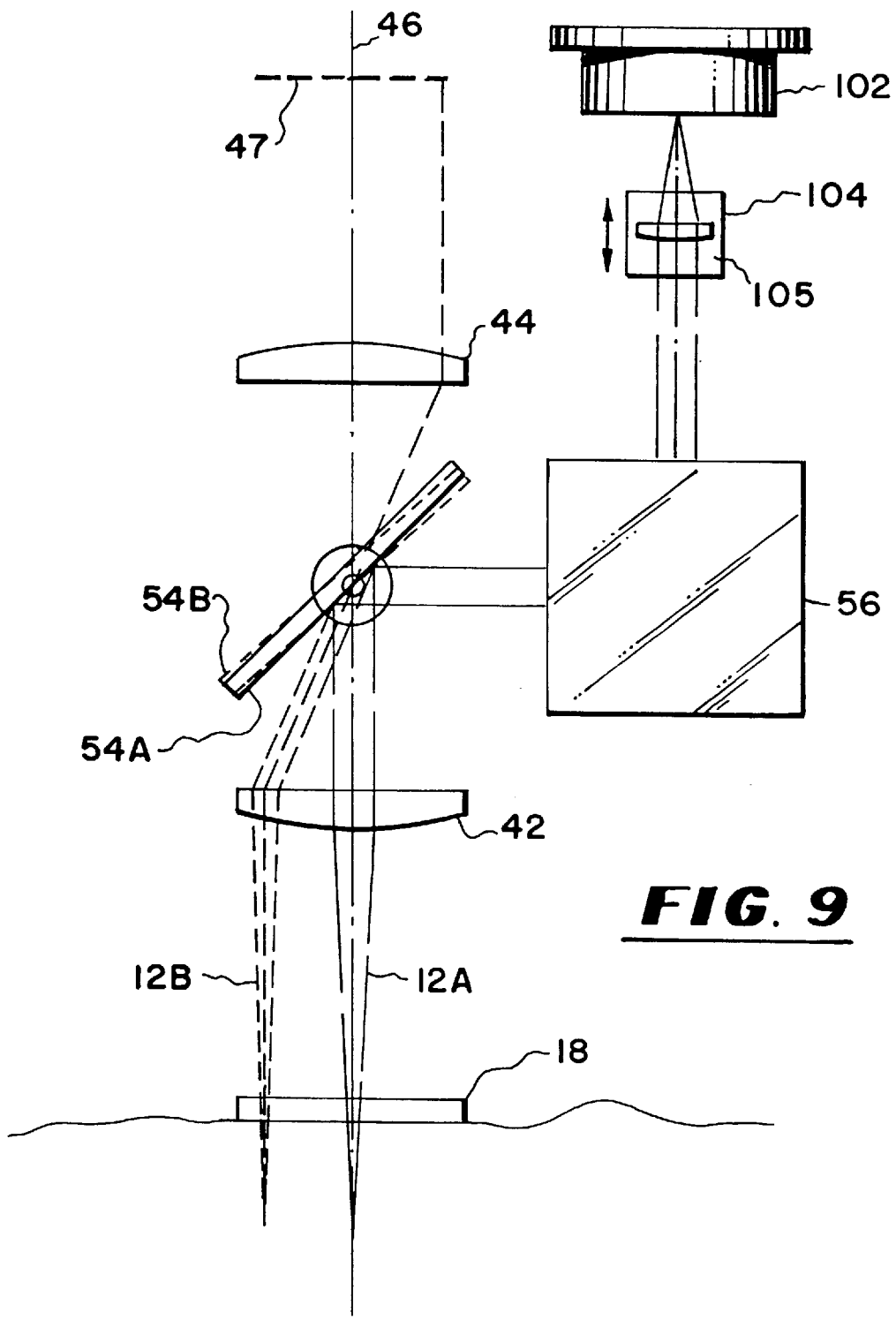

FIG. 8 is a block diagram of the electronics of the handpiece shown in FIG. 2; and FIG. 9 is an optical ray diagram illustrating the telecentric optical system of the instrument which is shown in the preceding figures, which, because it is telecentric, enables the area which is scanned to receive a beam, the central ray of which is generally parallel to the optical axis and to produce an image precisely corresponding to the area.

Figure 1:
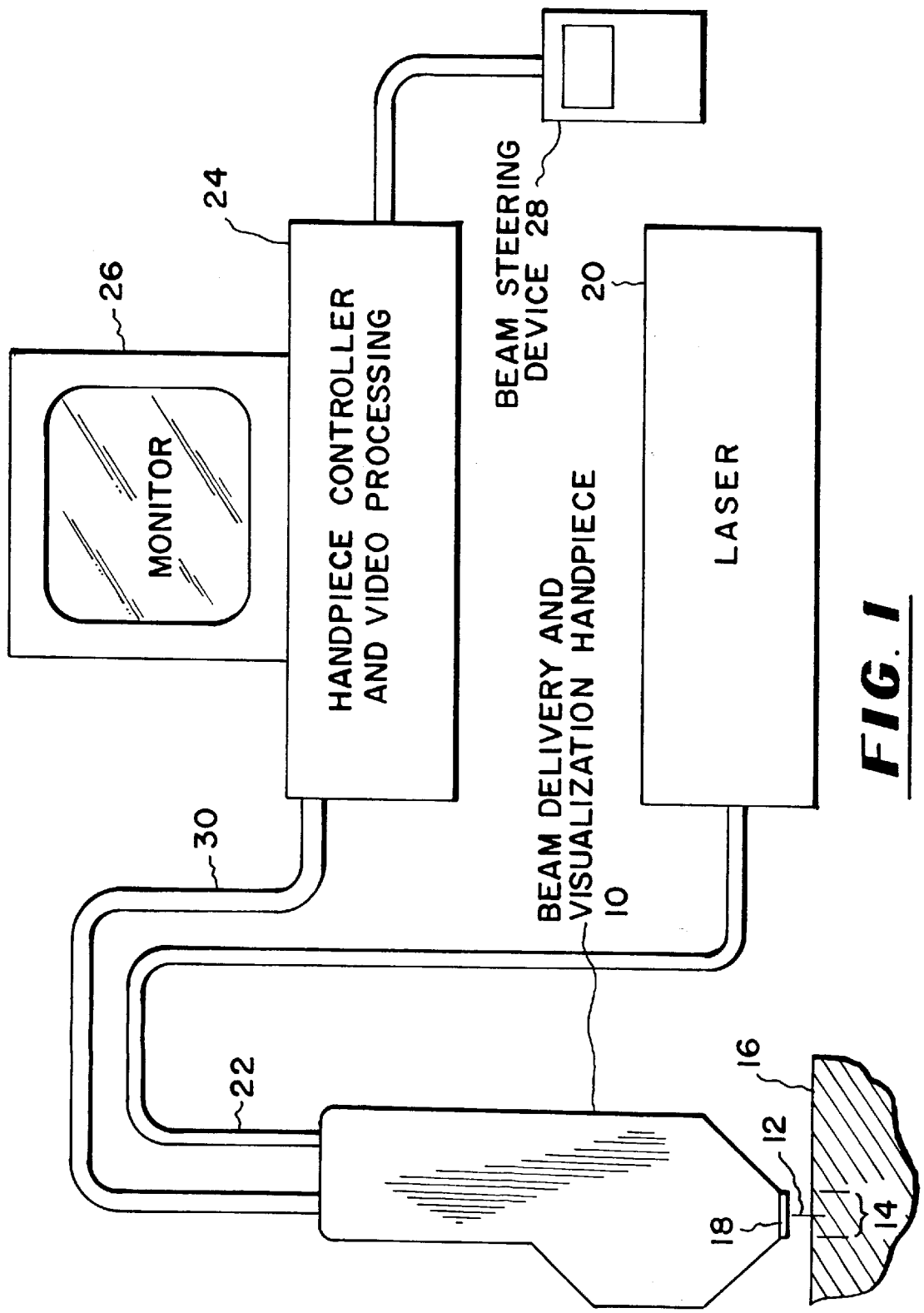
FIG. 1 is a block diagram illustrating a dermatological laser treatment system embodying the invention.

Referring to FIG. 1, a handpiece 10 contains the laser beam delivery and visualization means which projects and scans a laser beam 12 over an area 14 below the surface of the skin or other non-ocular tissue 16 of a patient requiring treatment. The beam is focused in the area at localized points to provide spots in the area at sites where photothermolysis treatment is required. This area may be in a plane generally perpendicular to the central ray of the beam 12. The plane is also generally parallel to a window 18 at the lower end of the handpiece 10 through which the beam projects. The beam may be scanned stepwise in rectangular or X-Y coordinates over the area 14 to the selected sites.

A feature of the invention is that the beam is focused, and particularly telecentrically focused using telecentric optics. The focus is in the plane of the area 14. Telecentric focusing insures that the central ray is perpendicular to the plane of the area 14. The ray is also parallel to the optical axis of the telecentric optics. A preferred form of the telecentric optics is described hereinafter in connection with FIGS. 3, 4 and 9.

The beam is preferably of a wavelength from 700 to 1300 nanometers (nm) where skin and other non-ocular tissues are translucent and where scattering occurs in the forward direction. Thus the light does not tend to reflect back into the tissue and pile up at the surface of the tissue. This minimizes collateral damage (reddening and even burning) of the skin or surface tissue outside of the treatment zone.

Focusing of the beam minimizes reddening and burning and limits the sites of photothermolysis to the spots in the area where the beam is focused. With a generally collimated or flooding type beam the upper layer of the skin can get hotter and can burn before a lesion (or other tissue at the treatment site) is affected by the laser energy. By focusing the beam, the energy penetrates the skin surface to the site to be treated without heating up the upper layers of the skin, since the intensity of the beam is lower in such upper layers than at the focal point. Thus heating of tissue which is in the path of the beam is minimized.

A laser 20 external of the handpiece 10 may be used to provide the optical treating energy. An optical fiber cable 22 delivers the energy from the laser to the handpiece.

The handpiece visualization means is provided by a video camera having a photoreceptor or sensor, preferably an X-Y matrix of CCD (Charge Couple Device) elements which are in a plane perpendicular to the optical axis of the telecentric optics and in a plane perpendicular to the axis. The central ray of the beam, as focused at the imaging or viewing (visualization) plane in which the photoreceptors are located then arrives perpendicular to the visualization plane. Parallax and similar distortion are avoided and a precise high resolution image is obtained with the video camera in the handpiece 10.

Electronics of the system provides a handpiece controller and video signal processor 24 for the camera. The video signals, after processing, may be displayed on a T.V. monitor 26. A cable 30, containing electrical wires connects the controller and processor 24 to the handpiece 10.

The beam is steered by a beam steering device 28 which may be a joystick, trackball or computer mouse type device. The controller 24 obtains signals from the beam steering device 28 and applies them to a beam deflection system utilizing mirrors and motors which step or steer the beam in X and Y directions. The beam deflection system is described in greater detail hereinafter in connection with FIGS. 3 and 4. The controller applies signals (pulses to the motors of the deflection means) to steer the beam in X and Y to the desired locations in the area 14. Automatically, these locations are focused in the visualization plane and an image is provided by the camera. In addition, the entire area may be flood illuminated, suitably by light containing spectral components of a wavelength which, like the wavelength of the laser beam, penetrates the skin without substantial scattering. The return (retroreflected) light, both from the spot where the laser beam is located and from the illumination, is incident on the visualization plane of the camera and an image of the area as well as of the spot where the beam is focused is obtained. From this image as viewed on the monitor the treating physician can steer the beam to the desired location.

The system is especially suitable for coagulation necrosis of spider veins or spider nevi. The nevi are visualized with visible light and the laser beam is tracked along the veins. The energy is then increased and regions along the vein are subject to photothermolysis. The vein is cut off and the pigment, usually blood, is eventually reabsorbed by the body of the patient.

To epilate using the system, the base of the hair follicle is visualized with an infrared illumination source and video camera and the laser spot positioned over the hair follicle. The laser is then operated, for example a shutter is placed to an open position, and a dose of optical energy of sufficient intensity is delivered at the follicle. With a nominal focal spot of 500 micrometers in diameter and a depth of focus of about 100 micrometers, a dose of about 25 Joules per centimeter squared ($J/cm^2$) is produced and the hair follicle and its adjacent blood vessels are destroyed by the heat produced by the absorbed laser energy (i.e. photothermolysis occurs). Because of the focusing of the beam, areas of tissue adjacent to the follicle are unaffected.

The controls and even video processing circuitry may be included in the handpiece 10. FIG. 2 shows a handpiece where the controls and video processing and even the video display (which provides the T.V. image for monitoring purposes) may be provided in the handpiece. FIG. 8 shows the electronic components for carrying out the control and video processing functions.

As shown in FIG. 2, the handpiece is adapted to be held by its distal or rear end 32 in the hand of the treating physician. This end 32 has a keypad with keys projecting from the surface of the housing for entry of laser control parameters, such as laser power, the duration of the laser bursts or pulses, and depth within the tissue of the focused spot as well as information as to the patient and the treatment afforded. In the position of the fore-finger, there is a trigger button which may operate the laser to turn it on and off and may also operate the shutter which controls the laser energy which is delivered through the window 18 at the proximal end of the handpiece 10. This trigger may be a two step switch which when depressed to the first step turns the laser on and to the second step actuates a motor which moves the shutter out of a position where it normally blocks the beam for safety purposes. The thumb of the operator may be used to manipulate a trackball 36 which operates an encoder of the type in a computer mouse and provides the beam steering control, and sends signals to the motors of the beam deflecting system.

A display such as a liquid crystal display may be used to present the image which is viewed by the camera, if an external monitor such as the monitor 26 is not used. The resolution obtained by such a display is less than may be desired for certain operations. Then an external large screen monitor 26 is more desirable. The display may also show the parameters which are entered by the keyboard such as laser power and pulse duration. A suitable operating laser power of ¼ watt and a suitable pulse duration (the duration of the burst of CW, IR laser energy) of ¼ second is indicated on the display 40.

Figure 3:
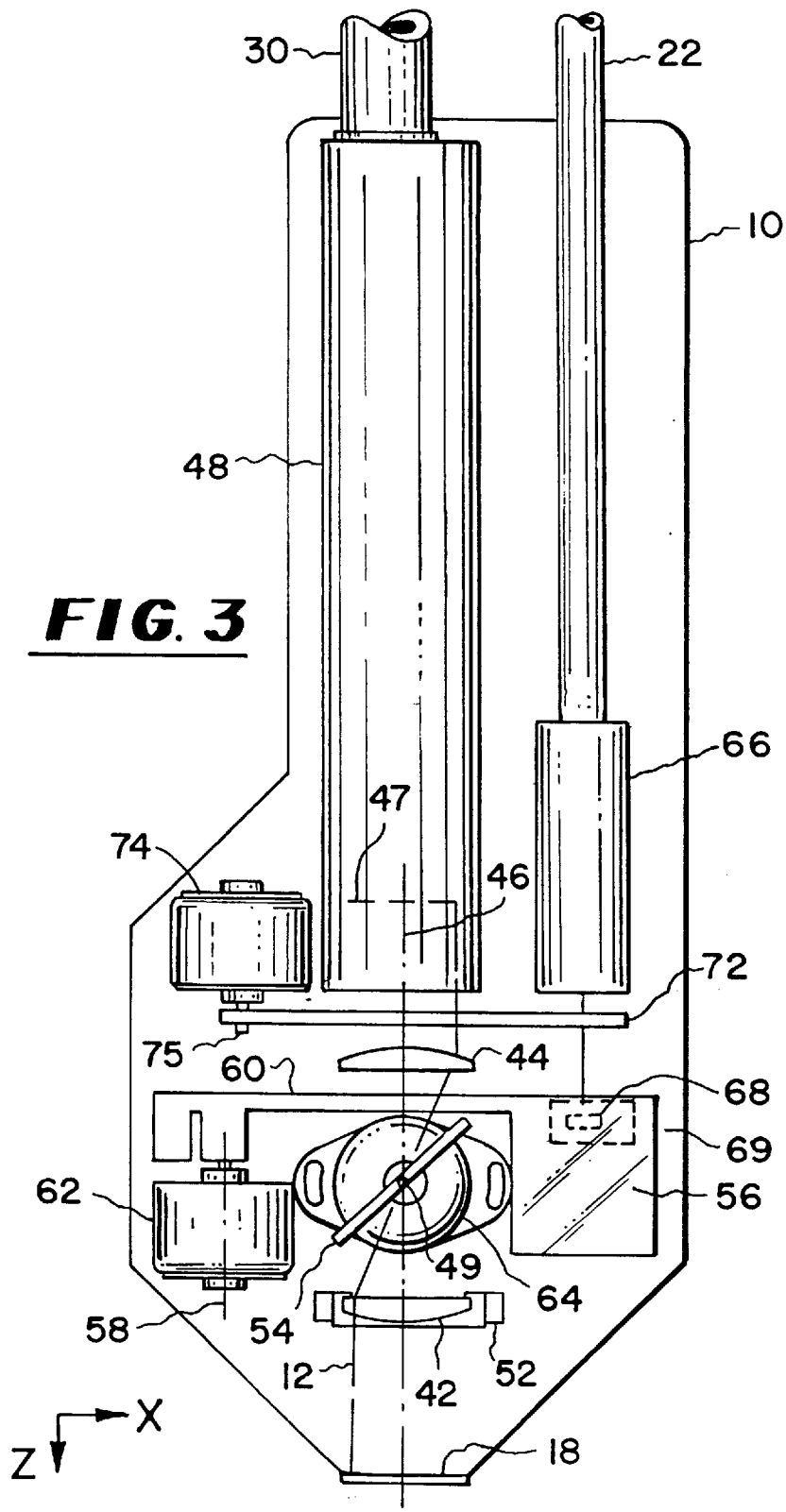
FIG. 3 is a diagram schematically showing the housing and internals of the handpiece illustrated in FIG. 3 when viewed from the front.
Figure 4:
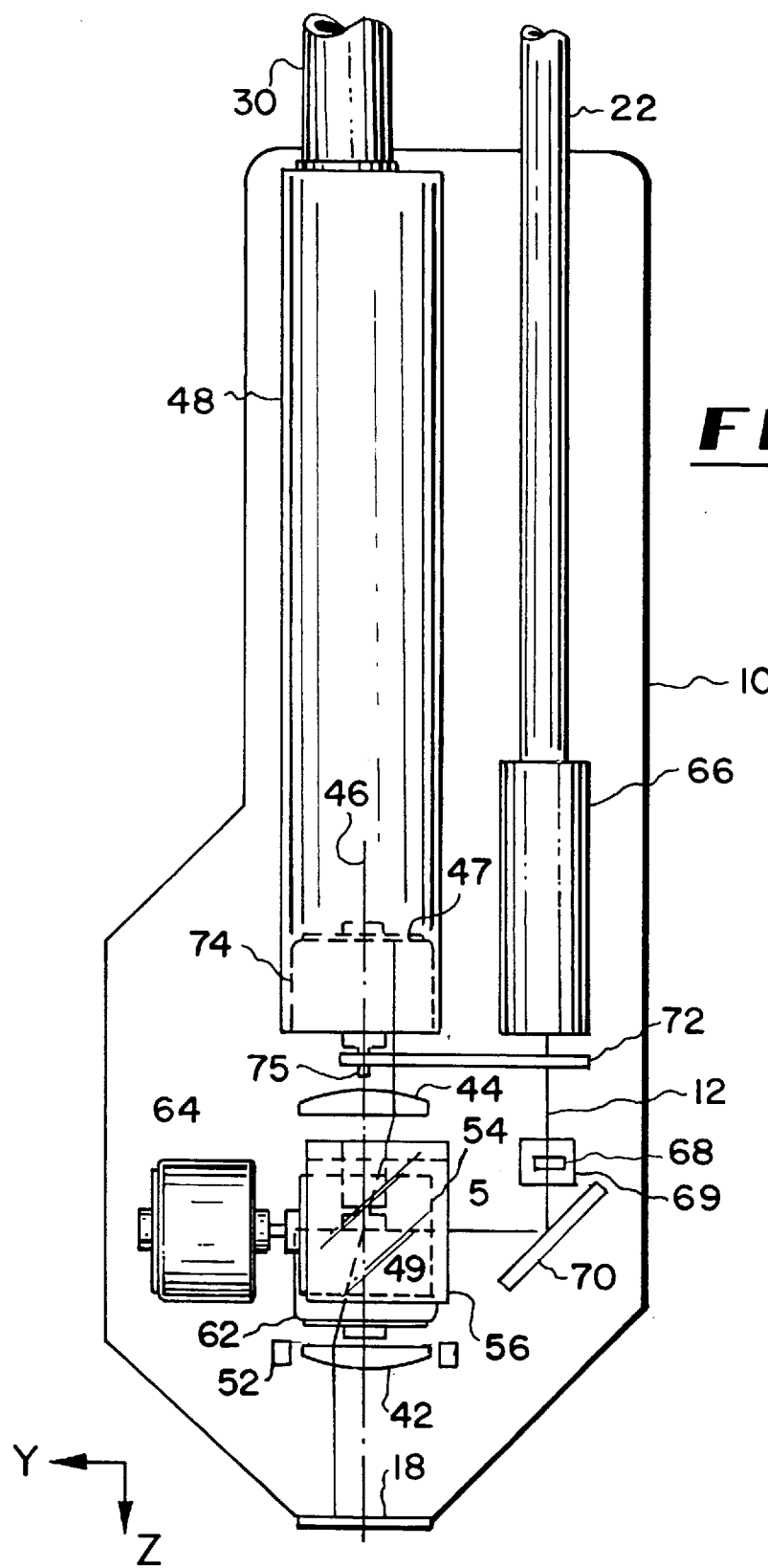
FIG. 4 is a view of the housing and the internals of the handpiece, but taken from the right side of FIG. 3.

Referring to FIG. 3, FIG. 4 and FIG. 9 there is shown a first lens 42 and a second lens 44 of telecentric optics. The optics has an optical axis 46 which provides a focus at the plane of the photoreceptors (the image or visualization plane) of a video camera 48. This camera is preferably a CCD camera having its matrix (an X-Y matrix) located in the image plane 47. The front or first lens 42 provides a front focus in the plane of the area under treatment (14—FIG. 1) and a rear focus midway between the back plane of the planoconvex lenses 42 and 44 (that is, the surface or side of these lenses which is planar).

The rear lens 44 has its front focus in the visualization plane 47 and its rear focus midway between the planar surfaces of the lenses 42 and 44. The midpoint focus is at 49 and intersects the optical axis 46. The focus 49 is the common rear and front focii of the lenses 42 and 44, respectively. Because the optics are telecentric, the central ray of the focused beam always remains perpendicular to the plane of the treatment area and the visualization plane 47, which are perpendicular to the optical axis 46, even as the beam is scanned over the treatment area. When the beam is retroreflected from the area it is focused in the visualization plane. The visualization plane also receives light which is returned through the telecentric lenses 42 and 44 and which is generated by an annular illuminating ring or lamp 52. This lamp has a broad spectrum of light but may contain a majority of its intensity in the infrared region including the wavelength of the laser light to allow visualization below the surface of the tissue. Then the entire area and even some of the surrounding area is visualized and an image thereof is obtained with the video camera 48.

The lenses 42 and 44 form part of the projection means, as does part of the beam deflection or steering means of the system. This deflection and steering means is provided by a first mirror 54 which has an axis of rotation perpendicular to the optical axis 46 and through mid focal point 49 of the lenses 42 and 44. Preferably, the deflecting or scan mirror 54 is a polarization beam splitter which reflects the incoming laser beam in a direction to propagate out of the handpiece 10 through the window 18. The return light has a component with an opposite sense of polarization and passes through the scan mirror 54 to the visualization plane 47.

The scan mirror 54 provides scanning over a first, say the X coordinate of the cartesian coordinates which define the length and width of the area under treatment. Another scan mirror 56 is rotatable about an axis 58. This mirror is tilted at an angle of approximately 45° such that a ray traveling parallel to the x-axis would be reflected into the plane of the diagram illustrated in FIG. 3.

The mirror 56 is carried by an arm 60 which is turned by the shaft (about the axis 58) of a galvanometer type motor 62, which may be a stepper motor. A similar motor 64 rotates the first scan mirror 54. The scan mirror 56 deflects the laser beam 12 along the other or Y coordinate. By controlling the motors 62 and 64, the beam may be located at any selected site in the treatment area and an image of the spot at the site is created at the visualization plane 47 of the camera 48. Thus, both steering and visualization is accomplished simultaneously and automatically. The two mirror steering or deflection system is generally of the type described in U.S. Pat. No. 5,048,904 issued Sep. 17, 1991 to J. I. Montague, which shows a two mirror scanner.

The laser energy is delivered by the optical fiber cable 22 to a fiber ferrule or coupler 66 from which the incoming beam projects and is focused by a lens 68. Lens 68 nominally collimates the beam. A focus mechanism 69, which may be either manual or electromechanical, sets the depth below the surface that the laser light is focused. The focus mechanism 69 moves lens 68 in the z direction relative to ferrule 66. The beam is folded at a fold mirror 70 and is directed to the polarization sensitive scan mirror 54. The beam is then focused by the front lens 42 of the telecentric optics to a spot in the area being treated which may be referred to as the treatment plane.

Focusing the beam increases the irradiance of the beam as it propagates to its nominal focus at the spot in the treatment plane. The half angle of convergence is equal to the arc sign of the numerical aperture of the lens 42 $\sin^{-1}$ (NA) where NA is the numerical aperture of the focused beam. After transmission through the window the half angle of convergence is reduced to $\sin^{-1}$ (NA/n), where n is the refractive index of the tissue. It may be desirable to use the window 18 as a contact plate. Then the material of the window is desirably of high thermal conductivity and is approximately matched to the refractive index of the skin or other tissue (n in the range of approximately 1.35 to 1.55).

Consider the case where the laser has a wavelength of 950 nm, the absorption coefficient of the tissue in the layers under the surface to the treatment area is $\mu_a$ a which is 0.1 $mm^{-1}$, the scattering coefficient $\mu'_s$ is 10 $mm^{-1}$. The tissue may have a anisotropy factor g of 0.985. The reduced scattering coefficient $\mu'_s$ is then 0.15 (i.e. the reduced scattering coefficent $\mu'_s = \mu_s$ (1−g). If the treatment area is 3 mm below the surface of the skin the approximate spot size considering scattering is about 500 micrometers. This is a size which is within the diameter of spider veins and approximately equal to the region at the base of a hair follicle. For a numerical aperture of the focused beam of 0.3, approximately 40% of the incident power from the coupler 66 is delivered in the treatment area. Because of the half angle of convergence the intensity is spread over a much larger area between the surface of the skin and the treatment area. It is believed that the safety margin for avoiding excessive heating which might cause surface tissue damage is 33% of the power delivered from the coupler 66, the beam focused with a lens having a numerical aperture of 0.3 provides a intensity or laser dose above the depth of focus at the treatment area (and the treatment plane) which is sufficient to avoid damage to the tissue above the treatment sites, in the foregoing example.

For personnel safety, protection of the camera 48 and for visualization a shutter 72 is provided by an arm which is rotated in a plane perpendicular to the optical axis 46 by a motor 74, which may be similar to the motors 62 and 64. This shutter 72 is shown in plan view in FIG. 5. The shutter has two sets (a, b, c and 1, 2, 3) of three regions which provide different transmisivity during different modes or stages of operation of the system. The normal or unpowered position of the shutter) is with the region 1 in the path of the retroreflective light to the visualization plane 47 in the camera and with the region a (a dense block or no hole at all through the shutter intercepting the output beam from the coupler 66. This dense block may preferably include a photodetector used to monitor the beam power eminating from ferrule 66. Then the illumination from the lamp 52 can be turned on and the area viewed. This mode or stage of operation may be used to move the instrument to find the desired area without any laser illumination.

When the area has been found the shutter is moved so that the incoming beam is intercepted at region b, containing a neutral density filter which attenuates the laser beam in the path of the output beam from the coupler 66. The region 2 is then in the path of the return light from the spot where the laser beam is focused in the treatment plane. The region 2 may be an open hole. This permits both visible viewing and viewing of the infrared (700 to 1300 nm wavelength illumination) due to the laser beam. In this position of the shutter the system utilizes the laser beam as a spotter or tracking beam to locate the sites to be treated, say a hair follicle or a part of a spider vein to be coagulated, or an adhesion between a tendon and its sheath.

Finally, the shutter is moved to its furtherest position (in a counter clockwise direction in FIG. 5) about the axis 70 of rotation of the shaft 75 of the motor 74. Then, the output beam 66 passes through an open hole c, while a neutral density filter (region 3) is interposed in the return path to protect the television camera (especially the CCD sensor array) during the treatment pulse.

Referring to FIGS. 6 and 7, a hand piece 100 is shown which is identical so far as its visualization and beam projection system is concerned and like parts are identified by like referenced numerals. An external laser is not used. Rather a laser diode 102 is used to produce the infrared radiation. The output of the diode is nominally colliminated by a lens 104 to provide a beam to the fold mirror 70 and thence to the deflection mirrors 56 and 54. The lens 104 mounted to focus mechanism 105, which may be manual or electromechanical, sets the depth below the surface of the tissue to which the laser light is focused. The electronics on which the laser diode 102 may be mounted and also which contains the controller and video processing circuitry is a printed circuit board 106. The components of the circuitry will be more apparent from FIG. 8.

From the foregoing description it will be apparent that there has been provided an improved system (method and apparatus) for microsurgical and especially dermatological treatment which enables visualization of the area being treated as well as provide safety for the patient and the user of the system. Variations and modifications in the herein described system, within the scope of the invention, and numerous other microsurgical procedures than described herein, will undoubtedly suggest themselves to those skilled in the art. Accordingly, the foregoing description should be taken as illustrative and not in a limiting sense.

We claim:

1. A system for thermolysis of dermatological tissue in an area under the surface thereof with visualization of said area which comprises a housing which is sufficiently small to be hand held, a window in said housing providing a port for illumination emanating from within said housing and disposed and in proximity to the tissue surface above said area, means for projecting a laser beam from said housing through said window, means in said projecting means for focusing said beam at selected locations in said area at spots sufficiently small in cross-section and of power and duration of said beam to cause localized thermolysis of the tissue at each of said spots, said projecting means also including means in said housing for deflecting said beam to locate each of said spots at each of said selected locations one at a time and stop said beam, and means in said housing for visualizing said area while said beam is deflected thereby verifying that each of said spots is at each of said selected locations.

2. The system according to claim 1 further comprising trigger means on said housing and projecting externally thereof for enabling the projection of said beam with sufficient power to cause thermolysis when it reaches said selected locations.

3. The system according to claim 1 further comprising means including a manual control projecting externally of said housing for operating said deflecting means and for steering said beam to said selected locations.

4. The system according to claim 1 further comprising means in said housing including a keyboard having keys projecting externally of said housing for entering data for control of beam parameters and information on patients being treated.

5. The system according to claim 1 wherein said laser beam is of a wavelength from about 700 to 1300 nm.

6. The system according to claim 5 wherein said tissue is skin and said area is up to 5 mm from the surface of the skin.

7. The system according to claim 6 wherein said laser beam is produced in a burst of about 0.25 second in duration and has the power of about 0.25 watts.

8. The system according to claim 1 wherein said projecting means for focusing and deflecting said beam to locate said spot at said selected locations comprises means which move said beam selectively along cartesian coordinates (X and Y) over said area and moving the focus of said beam along a Z axis perpendicular to a plane containing said X and Y coordinates.

9. The system according to claim 1 wherein said visualization means includes a T.V. camera in said housing and a T.V. monitor connected to said camera for providing T.V. pictures of said area.

10. The system according to claim 1 wherein said tissue comprises an inner layer of cells which defines spider veins, and said means in said projecting means including said focusing means which is operative to focus at said locations which are coincident with different ones of said veins to thermolyze regions of each of said veins containing endothelium cells in each of said veins which comprise said inner layer thereby causing each of said veins to collapse so that blood therein is reabsorbed by the patient's body.

11. The system according to claim 1 wherein said tissue is in the bulb of a hair follicle and said projecting means includes means operative to make at least one of said locations and said spot coincident with said follicle whereby said follicle is cauterized by said beam at said spot.

12. The system according to claim 1 wherein said visualizing means includes means for illuminating said area entirely with light which creates an image of said entire area while said projected beam is incident on said area so that said area and said spots can be visualized.

13. The system according to claim 1 further comprising adjustable focusing means operable upon said beam within said housing for controlling the depth of said area at which localized thermolysis occurs at each of said selected locations.

14. A system for thermolysis of dermatological tissue in an area under the surface thereof with visualization of said area and which system is sufficiently small to be hand held which comprises a housing, a window in said housing providing a port for illumination emanating from within said housing and disposed in proximity to the tissue surface above said area, means for projecting a laser beam from said housing through said window, means in said projecting means for focusing said beam at selected locations in said area at spots sufficiently small in cross-section and of power and duration of said beam to cause localized thermolysis of the tissue at said spot, said projecting means also including means in said housing for deflecting said beam to locate said spot at selected locations one at a time, and means in said housing for visualizing said area while said beam is deflected thereby verifying that said spot is at each of said selected locations, and further comprising telecentric optics having an optical axis extending through said window, said telecentric optics being included in said focusing and visualization means, a first image plane perpendicular to said axis in said housing and a second image plane containing said area, said telecentric optics projecting said illumination in a direction generally parallel to said optical axis and perpendicular to said first and second planes.

15. The system according to claim 14 wherein said visualizing means comprises a photoreceptor disposed in said first plane.

16. The system according to claim 15 wherein said visualizing means includes a CCD television camera having a sensor array providing said photoreceptor, said array being in said first plane.

17. The system according to claim 15 wherein said visualizing means further comprises a T.V. camera including said photoreceptor and a monitor for displaying a T.V. picture of the area imaged on said photoreceptor.

18. The system according to claim 14, wherein said deflecting means comprises a first mirror rotatable about an axis through said optical axis and perpendicular thereto for deflecting said beam along one of two cartesian coordinates (X and Y) to each of said selected locations, and a second mirror rotatable about a second axis for deflecting said beam towards said first mirror thereby deflecting said beam along the other of said coordinates to each of said selected locations, and said telecentric optics has a first lens disposed between said axis of rotation of said first mirror, which first lens focuses said beam at said first plane, and a second lens between said axis of first scan mirror and said second plane for focusing said beam at said second plane, said lenses also having common foci where said axis of rotation of said first mirror intersects said optical axis.

19. The system according to claim 18 wherein said visualizing means includes means for illuminating all of said area with light of a wavelength to which dermatological tissue is sufficiently transparent and which is transmitted by said lenses to provide an image for visualization.

20. The system according to claim 19 wherein said illumination means is a loop around a lens of said telecentric optics which faces said window.

21. A system for thermolysis of dermatological tissue in an area under the surface thereof with visualization of said area and which system is sufficiently small to be hand held, and which comprises a housing, a window in said housing providing a port for illumination generated within said housing and disposed in proximity to the tissue surface above said area, means for projecting a laser beam from said housing through said window, means in said projecting means for focusing said beam at selected locations in said area at spots sufficiently small in cross-section and of power and duration of said beam to cause localized thermolysis of the tissue at said spot, said projecting means also including means in said housing for deflecting said beam to locate said spot at selected locations one at a time, and means in said housing for visualizing said area while said beam is deflected thereby verifying that said spot is at each of said selected locations, and further comprising telecentric optics having an optical axis extending through said window, said telecentric optics being included in said focusing and visualization means, a first image plane perpendicular to said axis in said housing and a second image plane containing said area, said telecentric optics projecting said illumination in a direction generally parallel to said optical axis and perpendicular to said first and second planes, and wherein said deflecting means comprises a first mirror rotatable about an axis through said optical axis and perpendicular thereto for deflecting said beam along one of two cartesian coordinates to each of said selected locations, and a second mirror rotatable about a second axis for deflecting said beam towards said first mirror thereby scanning said beam along the other of said coordinates to each of said selected locations.

22. A system for thermolysis of dermatological tissue in an area under the surface thereof with visualization of said area, which system is sufficiently small to be hand held, which comprises a housing a window in said housing providing a port for illumination emanating from within said housing and disposed in proximity to the tissue surface above said area, means for projecting a laser beam from said housing through said window, means in said projecting means for focusing said beam at selected locations in said area at spots sufficiently small in cross-section and of power and duration of said beam to cause localized thermolysis of the tissue at said spot, said projecting means also including means in said housing for deflecting said beam to locate said spot at selected locations one at a time and to effect thermolysis due to the power, duration and cross-section of said beam at each of said spots, said projecting means also including means in said housing to locate said spot at said selected locations one at a time to effect thermolysis thereat, means in said housing for visualizing said area while said beam is deflected thereby verifying that each of said spots is at each of said selected locations, and wherein said tissue comprises an inner layer of cells which defines spider veins, and said means in said projecting means including said focusing means which is operative to focus at said selected locations which are coincident with different ones of said veins to thermolize regions of each of said veins containing endothelium cells in each of said veins which comprise said inner layer thereby causing each of said veins to collapse so that blood therein is reabsorbed by the patient's body, and wherein said projecting means includes means responsive to an image of said area for tracking said veins and enabling said laser beam to cause thermolysis of said veins at said locations as defined by said tracking means.

23. A system for thermolysis of dermatological tissue in an area under the surface thereof with visualization of said area which comprises, a housing sufficiently small to be hand held, a window in said housing providing a port for illumination generated within said housing and disposed in proximity to the tissues surface above said area, means for projecting a laser beam from said housing through said window, means in said projecting means for focusing said beam at selected locations in said area at spots sufficiently small in cross-section and of power and duration of said beam to cause localized thermolysis of the tissue at said spot, said projecting means also including means in said housing for deflecting said beam to locate said spot at selected locations one at a time, and means in said housing for visualizing said area while said beam is deflected thereby verifying that said spot is at each of said selected locations, and further comprising telecentric optics having an optical axis extending through said window, said telecentric optics being included in said focusing and visualization means, a first image plane perpendicular to said axis in said housing and a second image plane containing said area, said telecentric optics projecting said illumination in a direction generally parallel to said optical axis and perpendicular to said first and second planes, and wherein said projection means includes a shutter, means for moving said shutter so that different regions thereof selectively come into an intercepting relationship with said beam, said regions having separate beam blocking, attenuating and transmissive material in said different regions.

24. The system according to claim 23 wherein said regions which block, attenuate and transmit said beam are first regions of said shutter, and wherein said shutter has a plurality of second regions in the path of said beam upon retroflection thereof from said area, a first, a second and a third of said second regions respectively having a filter for blocking the wavelength of said beam, an opening for transmitting said retroreflected beam and a material which partially blocks and attenuates said retroreflected beam in intensity, said first and second regions which block light of the wavelength of said beam being arranged on said shutter to together intercept said projected and retroreflected beam, said first and second regions which attenuate and pass said projected and retroreflected beam being respectively arranged on said shutter together to intercept said projected and retroreflected beam, and said first and second regions which transmit and attenuate said projected and retroreflected beam, respectively, being arranged together to intercept said projected and retroreflected beam.

25. A system for thermolysis of dermatological tissue in an area under the surface of the skin with visualization of said area which comprises a housing which is sufficiently small to be hand held, a window in said housing providing a port for illumination generated within said housing and disposed in proximity to the skin above said area, means for projecting a laser beam from said housing through said window, means in said projecting means for focusing said beam at selected locations at spots where localized thermolysis of the tissue in the area at said spot is desired, said projecting means also including means in said housing for deflecting said beam to locate and stop said spot at said selected locations one at a time, means for irradiating said spots with sufficient power and over a sufficient duration to cause localized thermolysis of the tissue in said area at said spot, and means in said housing for visualizing all of said area while said beam is deflected thereby verifying said spot is stopped at each of said selected locations before irradiation of the tissue thereat.

26. The system according to claim 25 further comprising trigger means on said housing and projecting externally thereof for enabling the projection of said beam with sufficient power to cause thermolysis when it reaches said selected locations.

27. The system according to claim 25 wherein said projecting means for focusing and deflecting said beam to locate said spot at said selected locations comprises means which move said beam selectively along cartesian coordinates (X and Y) over said area and moving the focus of said beam along a Z axis perpendicular to a plane containing said X and Y_coordinates.

28. The system according to claim 25 wherein said tissue comprises an inner layer of cells which defines spider veins, and said means in said projecting means including said focusing means which is operative to focus at said locations which are coincident with different ones of said veins to thermolyze regions of each of said veins containing endothelium cells in each of said veins which comprise said inner layer thereby causing each of said veins to collapse so that blood therein is reabsorbed by the patient's body.

29. The system according to claim 25 wherein said tissue is in the bulb of a hair follicle and said projecting means includes means operative to make at least one of said locations and said spot coincident with said follicle whereby said follicle is cauterized by said beam at said spot.

30. The system according to claim 25 wherein said projection means includes a shutter having means for attenuating said beam to a power insufficient to cause localized thermolysis while said beam is being deflected to said selected locations and for transmitting said beam without substantial attenuation so that it achieves a power sufficient to cause said localized thermolysis when said beam is stopped at said spots at said selected locations.

* * * * *